US00PP35411P2

(12) United States Plant Patent
Bacon et al.

(10) Patent No.: US PP35,411 P2
(45) Date of Patent: Oct. 3, 2023

(54) GRAPEVINE PLANT NAMED 'SUGRA63'

(50) Latin Name: *Vitis vinifera*
Varietal Denomination: Sugra63

(71) Applicant: Sun World International, LLC, Bakersfield, CA (US)

(72) Inventors: Terry A. Bacon, Maplewood, NJ (US); Terrence J. Frett, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 18/102,949

(22) Filed: Jan. 30, 2023

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./207
CPC ..... A01H 5/08; A01H 5/00; A01H 6/88
See application file for complete search history.

(56) References Cited

U.S. PATENT DOCUMENTS

PP23,837 P3 * 8/2013 Sheehan ..... A01H 6/88 Plt./207
PP30,664 P3 * 7/2019 Bacon ..... A01H 6/88 Plt./207

* cited by examiner

*Primary Examiner* — June Hwu
(74) *Attorney, Agent, or Firm* — Knobbe, Martens, Olson & Bear, LLP

(57) ABSTRACT

The new variety of grapevine 'Sugra63' is characterized by the production of a large-sized, green and narrow elliptic berry with an early season ripening date. The berries of 'Sugra63' are very firm and very juicy.

1 Drawing Sheet

Latin name of the genus and species claimed: *Vitis vinifera.*

Variety denomination: 'SUGRA63'.

BACKGROUND AND SUMMARY OF THE INVENTION

This application relates to the discovery and asexual propagation of a new and distinct variety of grapevine, 'Sugra63', as herein described and illustrated. The new variety was first selected as breeder number 'GR972W' by Terry A. Bacon and Terrence J. Frett in Wasco, Kern County, Calif. in July 2020. The variety was originated by controlled hybridization.

The new variety 'Sugra63' is characterized by the production of a large-sized, green and narrow elliptic berry with an early-season ripening date. The berries of 'Sugra63' are very firm and very juicy.

The seed parent is 'GR473W' (unpatented) and the pollen parent is a bulk pollen mixture of four unpatented breeding selections: 'GR515W', 'GR518W', 'GR519W' and 'GR529W'. The parent varieties were first crossed in April 2016. The date of first sowing was March 2017, and the date of first flowering was April 2020.

The new variety 'Sugra63' was first asexually propagated in December 2020 in Wasco, Kern County, Calif., by Terry A. Bacon and Terrence J. Frett using hardwood cuttings.

The fruit of the new variety 'Sugra63' has green-colored skin like that of seed parent 'GR473W' (unpatented). The new variety 'Sugnar63' is distinguished from 'GR473W' in that the ripening of the new variety 'Sugra63' starts July 22 compared to August 18 for 'GR473W'. Further, the new variety 'Sugra63' also has a smaller berry weight, at 7.5 g, and cluster size, at 665 g, compared to a 9 g berry weight and 750 g cluster weight 'GR473W'.

The new variety 'Sugra63' can be distinguished from each of the four red grape varieties of the bulk pollen parent: 'GR515W', 'GR518W', 'GR519W' and 'GR529W'. The fruit of the new variety 'Sugra63' ripens later than the fruit of each of 'GR515W', 'GR518W', 'GR519W' and 'GR529W'. Further, the new variety 'Sugra63' has a larger cluster size at 665 g and a larger berry weight at 7.5 g, compared to a cluster size of 280 g and a berry weight of 4.9 g for 'GR518W,' a cluster size of 450 g and a berry weight of 5.3 g for 'GR518W,' and a cluster size of 425 g and a berry weight of 6.7 g for 'GR19W'. The new variety 'Sugra63 has a larger cluster size at 665 g compared to a cluster size of 550 g for 'GR529W' but a smaller berry weight of 7.5 g compared to 8 g for 'GR529W'. Additionally, the berries of the new variety 'Sugra63' are narrow elliptic compared to the obtuse ovate berries of 'GR515W,' 'GR518W,' and 'GR529W' and the broad elliptic berries of 'GR519W'.

The fruit of the new variety 'Sugra63' has a ripening time that is similar to that of 'Sheegene-21' (U.S. Plant Pat. No. 23,837), but the new variety 'Sugra63' has narrow elliptic berries, compared to the broad elliptic berries of 'Sheegene-21'. The new variety 'Sugnar63' is also distinguished from 'Sheegene-21' in that the new variety has a cluster weight of 665 g, compared to 600 g for 'Sheegene-21'.

The fruit of the new variety 'Sugra63' has a green narrow elliptic shape, similar to that of 'Sugrafiftytwo' (U.S. Plant Pat. No. 30,664). However, the new variety 'Sugra63' start ripening July 22, compared to July 4 for 'Sugafiftytwo'.

The fruit of the new variety 'Sugra63' has a green skin, similar to that of 'IFG Ten' (U.S. Plant Pat. No. 24,583).

However, the fruit of the new variety 'Sugra63' starts ripening July 22, compared to August 13 for 'IFG Ten'. Additionally, the new variety 'Sugar63' has narrow elliptic berries, compared to broad elliptic berries for 'IFG Ten'.

The fruit of the new variety 'Sugra63' has a green skin like that of 'Sugraone' (U.S. Plant Pat. No. 3,106), but ripening of the berries of the new variety 'Sugra63' begins earlier on July 22, compared to July 15 for 'Sugraone'. Additionally, the new variety 'Sugar63' has narrow elliptic berries, compared to broad elliptic berries for Sugraone'.

The new 'Sugra63' variety has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration taken from a 3-year-old plant shows typical specimens of the foliage and fruit of the present new grape variety 'Sugra63'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 1986.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to three-year-old 'Sugra63' plants grown in the vicinity of Wasco, Kern County, Calif. during 2022, and is believed to apply to plants of the variety grown under similar conditions of soil and climate elsewhere.

VINE

General: (Measurements taken on a three-year-old plant).

- *Vine size*.—Large. Height: Approximately 2.0 m. Width: Approximately 2.5 m.
- *Vigor*.—Medium-high.
- *Density of foliage*.—Dense.
- *Productivity*.—Very productive.
- *Crop load*.—Approximately 30 kg per vine after thinning.
- *Own root*.—Yes.
- *Training method*.—Typically spur pruned leaving about 40 2-bud spurs.
- *Resistance*.—Neither resistance nor susceptibility to particular diseases or pests has been observed in this variety.

Trunk:

- *Shape*.—Stocky.
- *Diameter*.—Approximately 7.8 cm (at 30 cm above the soil line).
- *Straps*.—Short.
- *Surface texture*.—Medium shaggy.
- *Inner and outer bark color*.—Inner bark about Medium Greyed-Orange 166C and weathering to about Dark Greyed-Green 197B in the outer bark.

SHOOTS

Young shoot:

- *Form of tip*.—Half open.
- *Intensity of anthocyanin coloration of tip*.—Absent or very sparse.
- *Density of prostrate hairs on tip*.—Absent or very sparse.
- *Density of erect hairs on tip*.—Absent or very sparse.
- *Color*.—About Medium Green 139C.

Woody shoot (observations made in the middle third of shoot):

- *Attitude before tying*.—Semi-drooping.
- *Growth of axillary shoots*.—Medium, about 19 to 25 cm in length.
- *Internode length*.—Short, approximately 70 mm.
- *Width at node*.—Approximately 10 mm.
- *Cross section*.—Circular.
- *Surface texture*.—Striated.
- *Main color*.—About Medium Greyed-Orange 166D.
- *Color of dorsal side of internode*.—About Medium Greyed-Orange 166D.
- *Color of ventral side of internode*.—About Medium Greyed-Orange 166D.
- *Color of dorsal side of node*.—About Medium Greyed-Orange 166D.
- *Color of ventral side of node*.—About Medium Greyed-Orange 166D.
- *Density of erect hairs on nodes*.—Absent.
- *Density of erect hairs on internodes*.—Absent or Very Sparse.
- *Density of prostrate hairs on internodes*.—Absent or Very Sparse.
- *Density of prostrate hairs on nodes*.—Absent or Very Sparse.

Tendrils:

- *Distribution on the shoot at full flowering*.—Continuous.
- *Thickness*.—Approximately 3 mm.
- *Color*.—About Light Green 141D in mid-summer.
- *Form*.—Bifurcated.
- *Number of consecutive tendrils*.—About 2.
- *Length of tendril*.—Medium, approximately 14 cm.

LEAVES

Young Leaves:

- *Color of upper surface of first 4 distal unfolded leaves*.—About Medium Green 143C.
- *Average intensity of anthocyanin coloration of six distal leaves prior to flowering*.—Absent or very slight.

*Density of prostrate hairs between veins at lower surface of 4th distal unfolded leaf.*—Absent or very sparse.

*Density of erect hairs between veins at lower surface of 4th distal unfolded leaf.*—Absent or very sparse.

*Density of prostrate hairs on veins at lower surface of 4th distal unfolded leaf.*—Absent or very sparse.

*Density of erect hairs on veins at lower surface of 4th distal unfolded leaf.*—Absent or very sparse.

Mature leaves (observations made in the middle third of shoot):

*Size.*—Medium.

*Average length.*—Approximately 9 cm without petiole.

*Average width.*—Approximately 12 cm without petiole.

*Shape of blade.*—Pentagonal.

*Number of lobes.*—Approximately 5.

*Mature leaf profile.*—Undulate.

*Blistering surface of blade upper surface.*—Absent or very weak.

*Leaf blade tip.*—In the plane of the leaf.

*Undulation of margin.*—Slightly undulating.

*Thickness.*—Average — typical of *Vitis vinifera* species.

*Overall shape of teeth.*—Mixture of both sides straight and both sides convex.

*Length of teeth.*—Medium, ranging from about 5 mm to 10 mm, usually 6 mm.

*Ratio length/width of teeth.*—Very small, nearly 1:1.

*General shape of petiole sinus lobes.*—Wide open.

*Tooth at petiole sinus.*—Absent.

*Petiole sinus limited by veins.*—Absent.

*Shape of upper lateral sinus lobes.*—Slightly overlapping.

*Depth of upper lateral sinuses.*—Deep, approximately 4 cm to 6 cm.

*Density of prostrate hairs between veins on lower surface of blade.*—Absent to very sparse.

*Density of erect hairs between veins on lower surface of blade.*—Absent to very sparse.

*Density of prostrate hairs on main veins on lower surface of blade.*—Absent to very sparse.

*Density of erect hairs on main veins on lower surface of blade.*—Absent to very sparse.

*Density of prostrate hairs on main veins on upper surface of blade.*—Absent to very sparse.

*Autumn coloration of leaves.*—Usually about Light Green 138B becoming about Medium Grey-Brown 199C.

Upper leaf surface:

*Color.*—About Dark Green 141A.

*Surface texture.*—Smooth.

*Surface appearance.*—Dull.

*Anthocyanin coloration of main veins.*—Absent or very sparse.

Lower leaf surface:

*Color.*—About Light Green 142C.

*Surface texture.*—Smooth.

*Surface appearance.*—Dull.

*Anthocyanin coloration of main veins.*—Absent or very low.

Petiole:

*Length of petiole.*—Approximately 6 cm.

*Diameter.*—Approximately 3 mm.

*Length of petiole compared to middle vein.*—Mostly equal; 6 cm for the petiole, compared to 6 cm for middle vein.

*Density of prostrate hairs on petiole.*—Absent.

*Density of erect hairs on petiole.*—Absent.

*Color.*—About Medium Greyed-Orange 172C.

Buds:

*Shape.*—Conical.

*Size.*—Medium, approximately 3 mm wide×4 mm long.

*Position.*—Slightly held out.

*Bud fruitfulness.*—Basal, mostly fruitful.

*Time of bud burst.*—Early, approximately March 6th for the southern San Joaquin Valley region of California.

FLOWERS

General:

*Flower type.*—Fully developed stamen and fully developed gynoecium.

*Position of first flowering node.*—Usually $5^{th}$ node of current season growth.

*Number of inflorescences per shoot.*—Averages 1.5.

*Time of full bloom.*—Approximately April 27th in the southern San Joaquin Valley region of California.

FRUIT

General:

*Ripening period.*—Early season, beginning about July 22nd in the southern San Joaquin Valley region of California.

*Use.*—Fresh market.

*Storage quality.*—Excellent.

Cluster:

*Form.*—Broadly conical, shouldered.

*Cluster size (peduncle excluded).*—Large.

*Cluster length (peduncle excluded).*—Approximately 21 cm.

*Cluster width.*—Approximately 18 cm.

*Cluster weight.*—Approximately 665 g.

*Cluster density.*—Medium, loose-full.

*Number of berries.*—Approximately 90 berries after tipping.

Peduncle:

*Length.*—Long, approximately 3 cm.

*Diameter.*—Approximately 5 mm.

*Lignification of peduncle.*—Weak.

*Color.*—About Medium Green 143B.

Berry:

*Size.*—Large, approximately 7.5 g.

*Dimensions.*—Width: Approximately 21 mm. Length: Approximately 30 mm.

*Uniformity of size.*—Somewhat uniform.

*Shape.*—Narrow elliptic.

*Cross section.*—Circular.

*Skin color (without bloom).*—About Medium Green 140B.

*Flesh color.*—About Light Grenn142B.

*Anthocyanin color of flesh.*—Absent or very weak.

*Bloom (cuticular wax).*—Medium, typical of most commercial *Vitis vinifera.*

*Pedicel length.*—Approximately 11 mm.

*Pedicel thickness.*—Medium, approximately 1.2 mm.

*Berry separation from pedicel.*—Moderately easy.

*Seed traces*.—Rudimentary.
*Berry firmness*.—Very firm.
*Flesh juiciness*.—Very juicy.
*Flesh texture*.—Very crunchy and juicy.
*Particular flavor*.—Slightly Muscat.
*Refractometer test*.—About 18 Brix.
*Juice pH*.—About 3.56.
*Titratable acidity*.—About 0.61%.
*Brix:acid ratio*.—Approximately 29.5.

Skin:
*Skin thickness*.—Medium, about 175 μm.
*Skin texture*.—Smooth.
*Skin reticulation*.—Absent.
*Skin tenacity*.—Tenacious to flesh.
*Skin tendency to crack*.—Rare.
*Skin sensitivity to sunburn*.—None.

What is claimed is:

1. A new and distinct variety of grapevine plant named 'SUGRA63' as herein illustrated and described.

* * * * *

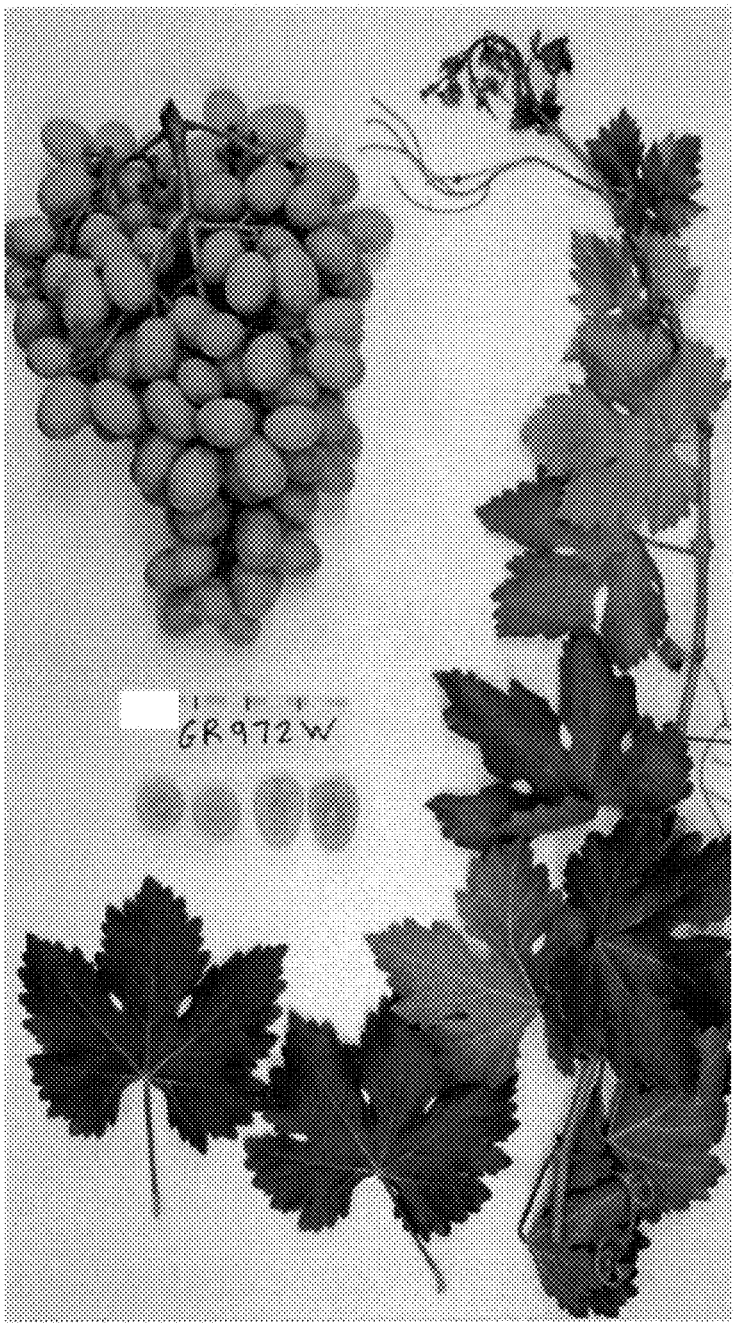
GR972W